United States Patent
Xiao et al.

(10) Patent No.: US 11,890,182 B2
(45) Date of Patent: Feb. 6, 2024

(54) COATED STENT

(71) Applicant: Shenzhen Lifetech Endovascular Medical Co., Ltd., Shenzhen (CN)

(72) Inventors: Benhao Xiao, Shenzhen (CN); Wenjun Pu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 212 days.

(21) Appl. No.: 17/297,229

(22) PCT Filed: Nov. 22, 2019

(86) PCT No.: PCT/CN2019/120102
§ 371 (c)(1),
(2) Date: May 26, 2021

(87) PCT Pub. No.: WO2020/108389
PCT Pub. Date: Jun. 4, 2020

(65) Prior Publication Data
US 2022/0023074 A1    Jan. 27, 2022

(30) Foreign Application Priority Data

Nov. 27, 2018    (CN) .......................... 201811425415.8

(51) Int. Cl.
*A61F 2/07* (2013.01)
*A61F 2/915* (2013.01)
*A61F 2/82* (2013.01)

(52) U.S. Cl.
CPC ................ *A61F 2/07* (2013.01); *A61F 2/915* (2013.01); *A61F 2002/075* (2013.01);
(Continued)

(58) Field of Classification Search
None
See application file for complete search history.

(56) References Cited

U.S. PATENT DOCUMENTS

| | | | |
|---|---|---|---|
| 2001/0023369 A1* | 9/2001 | Chobotov | A61F 2/06 623/1.11 |
| 2005/0113933 A1 | 5/2005 | Carter et al. | |
| 2018/0008394 A1* | 1/2018 | Marmur | A61F 2/07 |

FOREIGN PATENT DOCUMENTS

| | | | | |
|---|---|---|---|---|
| CN | 106983581 A | * | 7/2017 | .............. A61F 2/07 |
| EP | 3 075 352 A1 | | 10/2016 | |

OTHER PUBLICATIONS

Machine translation of the description of CN106983581A from Espacenet patent search (https://worldwide.espacenet.com/patent/search/family/059416325/publication/CN106983581A?q=cn106983581a). Accessed Feb. 21, 2023. (Year: 2023).*

(Continued)

*Primary Examiner* — Rebecca S Preston
(74) *Attorney, Agent, or Firm* — Raymond Sun (57) ABSTRACT

A coated stent (100,200,300,400), comprises a coated unit (110,210,310,410), and an exposed unit (120,220,320,420) which is a ring-shaped structure and which is provided on the periphery (113,213,313) of an end portion (112,212,312) of the coated unit (110,210,310,410); the exposed unit (120,220,320,420) comprises an inward-tilting wave body (122,222,322,422), the inward-tilting wave body (122,222, 322,422) comprising at least a first wave crest (122a,222a, 322a) and a first wave rod (122c) connected to the first wave crest (122a,222a,322a); the position of the first wave crest (122a.222a,322a) is farther away from the coated unit (110,210,310,410) than other positions on the inward-tilting wave body (122,222,322,422); the first wave rod (122c) is planar, and from the first wave crest (122a,222a,322a) to an end of the exposed unit (120,220,320,420) near the coated unit (110,210,310,410), the radial distance from the inward-tilting wave body (122,222,322,422) to the central axis (102,202,302,402) of the coated unit (110,210,310,410) gradually increases. When the coated stent (100,200,300,

(Continued)

400) is implanted into an arterial vessel (10), the inward-tilting wave body (122,222,322,422) forms a certain avoidance space due to the tilt to adapt to the curvature of a large curved side (11) of the arterial vessel (10), and prevents the inward-tilting wave body (122,222,322,422) from directly piercing a branch vessel (20).

15 Claims, 10 Drawing Sheets (52) U.S. Cl.
 CPC .. *A61F 2002/825* (2013.01); *A61F 2220/0008* (2013.01); *A61F 2250/0037* (2013.01); *A61F 2250/0039* (2013.01)

(56) References Cited

OTHER PUBLICATIONS

Machine translation of the description of CN108261253A from Espacenet patent search (https://worldwide.espacenet.com/patent/search/family/062771118/publication/CN108261253A?q=cn108261253A). Accessed Feb. 21, 2023. (Year: 2023).*
International Search Report dated Feb. 7, 2020 for corresponding PCT Application No. PCT/CN2019/120102.
Office Action dated Mar. 14, 2022 for corresponding India Application No. 202127027769.
Office Action dated Jan. 1, 2020 for corresponding China Application No. 201811425415.8.
Office Action dated Sep. 28, 2020 for corresponding China Application No. 201811425415.8.
Office Action dated Mar. 29, 2021 for corresponding China Application No. 201811425415.8.
First Office Action dated Jan. 6, 2020 for corresponding China Application No. 201811425415.8 and Translation.
Response to First Office Action dated Jan. 6, 2020 for corresponding China Application No. 201811425415.8 and Translation.
Second Office Action dated Sep. 28, 2020 for corresponding China Application No. 201811425415.8 and Translation.
Response to Second Office Action dated Sep. 28, 2020 for corresponding China Application No. 201811425415.8 and Translation.
Amended Claims in Response to Second Office Action dated Sep. 28, 2020 for corresponding China Application No. 201811425415.8 and Translation.
Third Office Action dated Mar. 29, 2021 for corresponding China Application No. 201811425415.8 and Translation.
Response to Third Office Action dated Mar. 29, 2021 for corresponding China Application No. 201811425415.8 and Translation.
Notice of Grant dated Jun. 21, 2021 for corresponding China Application No. 201811425415.8 and Translation.
European Search Report dated Aug. 5, 2022 for corresponding EP 19 88 9519.

* cited by examiner

COATED STENT

FIELD

The present disclosure relates to the technical field of medical devices, and particularly relates to a covered stent.

BACKGROUND

A thoracic aortic aneurysm refers to an aneurysm that occurs in the aortic sinus, ascending aorta, aortic arch or descending aorta, and the aneurysm causes local or multiple outward irreversible dilatation or bulging of the thoracic aorta. Generally, a covered stent is implanted into a blood vessel through a sheath, and the covered stent completely isolates an aortic aneurysm from blood by means of the principle of endovascular exclusion; that is, the covered stent isolates an aortic aneurysm site to reconstruct a blood flow channel, so that the aneurysm is thrombosed or muscularized to achieve the purpose of therapy.

However, for a traditional covered stent, its bare section easily stimulates and compresses a branch vessel connected with an arterial vessel, and can even puncture the branch vessels, resulting in new lesions such as life-threatening dissection. Meanwhile, the difficulty in mounting the covered stent into the sheath and releasing the covered stent from the sheath is also increased.

SUMMARY

One technical problem to be solved by the present disclosure is how to prevent a covered stent from stimulating a branch vessel.

A covered stent, including:

a covered unit; and a bare unit, which is a ring-shaped structure and arranged on a periphery of an end portion of the covered unit, and the bare unit includes an inward-tilting wave body including a first wave crest, a first wave trough, and a first wave rod connecting the first wave crest with the first wave trough, a vertex of the first wave trough is located on the periphery of the end portion of the covered unit close to the bare unit, the first wave crest is further from the covered unit than the first wave trough, the first wave rod is planar, and from the first wave crest to the first wave trough, a radial distance from the inward-tilting wave body to a central axis of the covered unit gradually increases.

A technical effect of one embodiment of the present disclosure is as follows: from the first wave crest to an end of the bare unit close to the covered unit, the radial distance from the inward-tilting wave body to the central axis of the covered unit gradually increases. After the covered stent is implanted into an arterial vessel, the inward-tilting wave body forms a certain avoidance space due to the tilting, so as to adapt to the curvature of a large curved side of the arterial vessel, avoids stimulation and compression on the branch vessel, and prevents the inward-tilting wave body from directly puncturing the branch vessel. Meanwhile, sheathing and releasing of the covered stent are facilitated.

DETAILED DESCRIPTION OF THE INVENTION

In order to facilitate the understanding of the present disclosure, the present disclosure will be described more comprehensively below with reference to relevant drawings. Preferred embodiments of the present disclosure are given in the drawings. However, the present disclosure may be implemented in many different forms, and is not limited to the embodiments described herein. Conversely, the purpose of providing these embodiments is to make the disclosure of the present invention more thorough and comprehensive.

It should be noted that when one element is referred to as being "fixed" to another element, the element may be directly located on the other element or an intermediate element may also be present. When one element is considered to be "connected" to other element, the element may be directly connected to the other element or an intermediate element may be present at the same time. The terms "inner", "outer", "left", "right" and the like used herein are for illustrative purposes only, and are not meant to be the only embodiments.

Referring to FIGS. 1 to 5, the present disclosure provides a covered stent 100, including a covered unit 110 and a bare unit 120, wherein the bare unit 120 is a ring-shaped structure and arranged on a periphery of an end portion of the covered unit 110. A surface of the covered unit 110 is covered with a membrane to form a tubular structure with two open ends and a closed middle, and when the entire covered stent 100 is implanted in an arterial vessel 10, the membrane on the covered unit 110 plays a role in isolating an aortic aneurysm on the arterial vessel 10 from blood. The bare unit 120 is not covered with a membrane. The bare unit 120 includes an inward-tilting wave body 122 that includes at least a first wave crest 122a and a first wave rod 122c connected to the first wave crest 122a; the first wave crest 122a is further from the covered unit 110 than other positions of the inward-tilting wave body 122; the first wave rod 122c is planar, and from the first wave crest 122a to the end of the bare unit 120 that is closer to the covered unit 110, the radial distance from the inward-tilting wave body 122 to a central axis of the covered unit gradually increases. For example, the first wave rod 122c is linear. In this embodiment, the bare unit 120 includes only a wave ring 101 formed by winding a metal wire, the wave ring 101 of the bare unit 120 includes the inward-tilting wave body 122, the inward-tilting wave body 122 is arranged on a periphery 113 of an end portion 112 of the covered unit 110, the inward-tilting wave body 122 includes a first wave crest 122a, a first wave trough 122b and a first wave rod 122c for connecting the first wave crest 122a with the first wave trough 122b, with a vertex of the first wave trough 122b located on the periphery 113 of the end portion 112 of the covered unit 110 close to the bare unit 120; the first wave crest 122a is further from the covered unit 110 than the first wave trough 122b, the first wave rod 122c is planar, and from the first wave crest 122a to the first wave trough 122b, a radial distance from the inward-tilting wave body 122 to a central axis of the covered unit 110 gradually increases, that is, the inward-tilting wave body 122 itself does not bend, but tilts inwardly as a whole. According to one embodiment, the inward-tilting wave body 122 is inclined toward the central axis 102 of the covered unit 110 by a set angle α.

Figure 1:
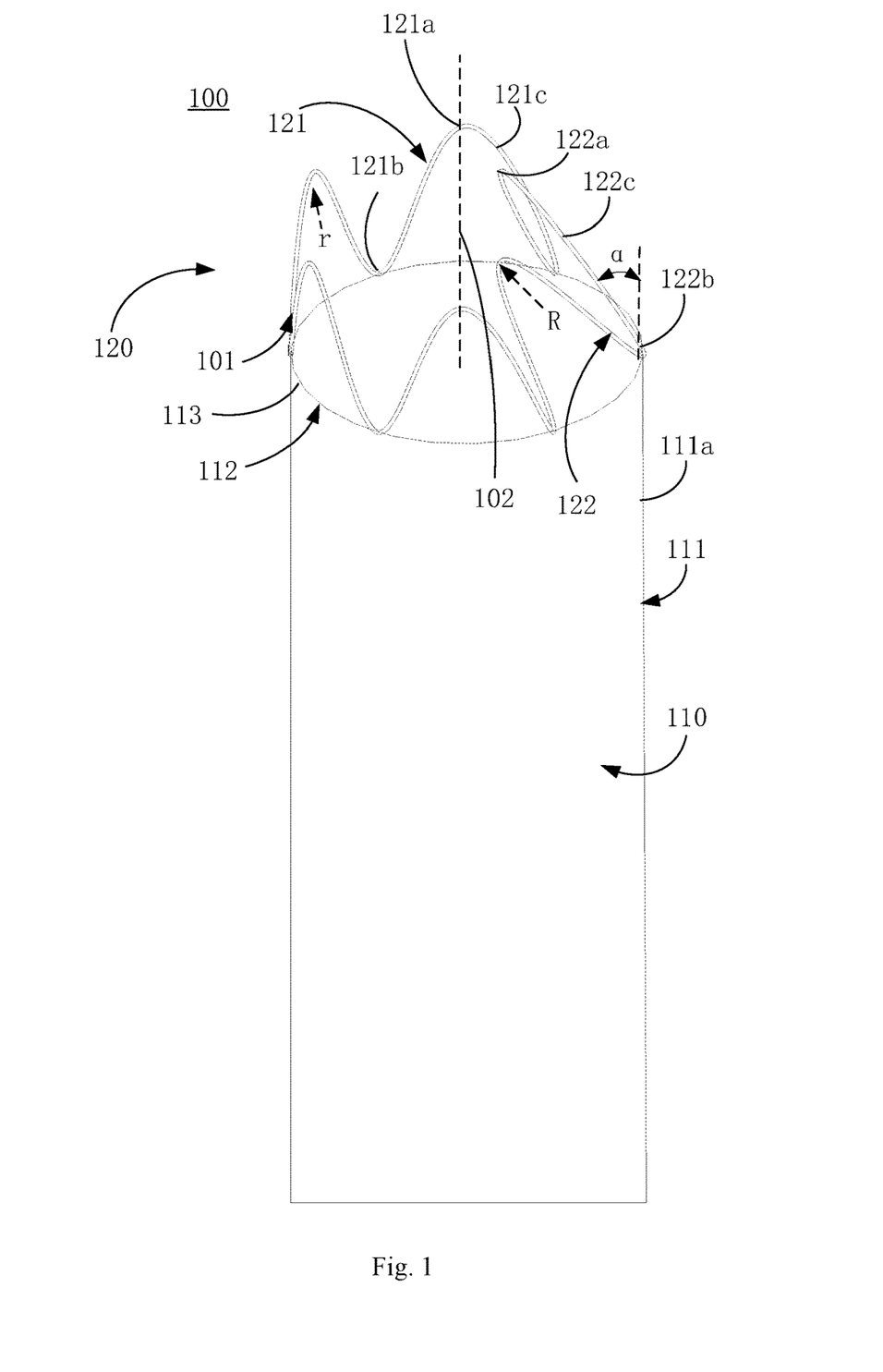
FIG. 1 is a schematic structural diagram of a covered stent according to a first embodiment.

It should be noted that the bare unit 120 may not be a complete wave ring; that is, the end of the wave trough of the first wave ring that located at the end of the covered stent 100 is covered with a membrane. The part not covered with the membrane is the bare unit 120, and the part covered with the membrane is the covered unit 110.

Figure 4:
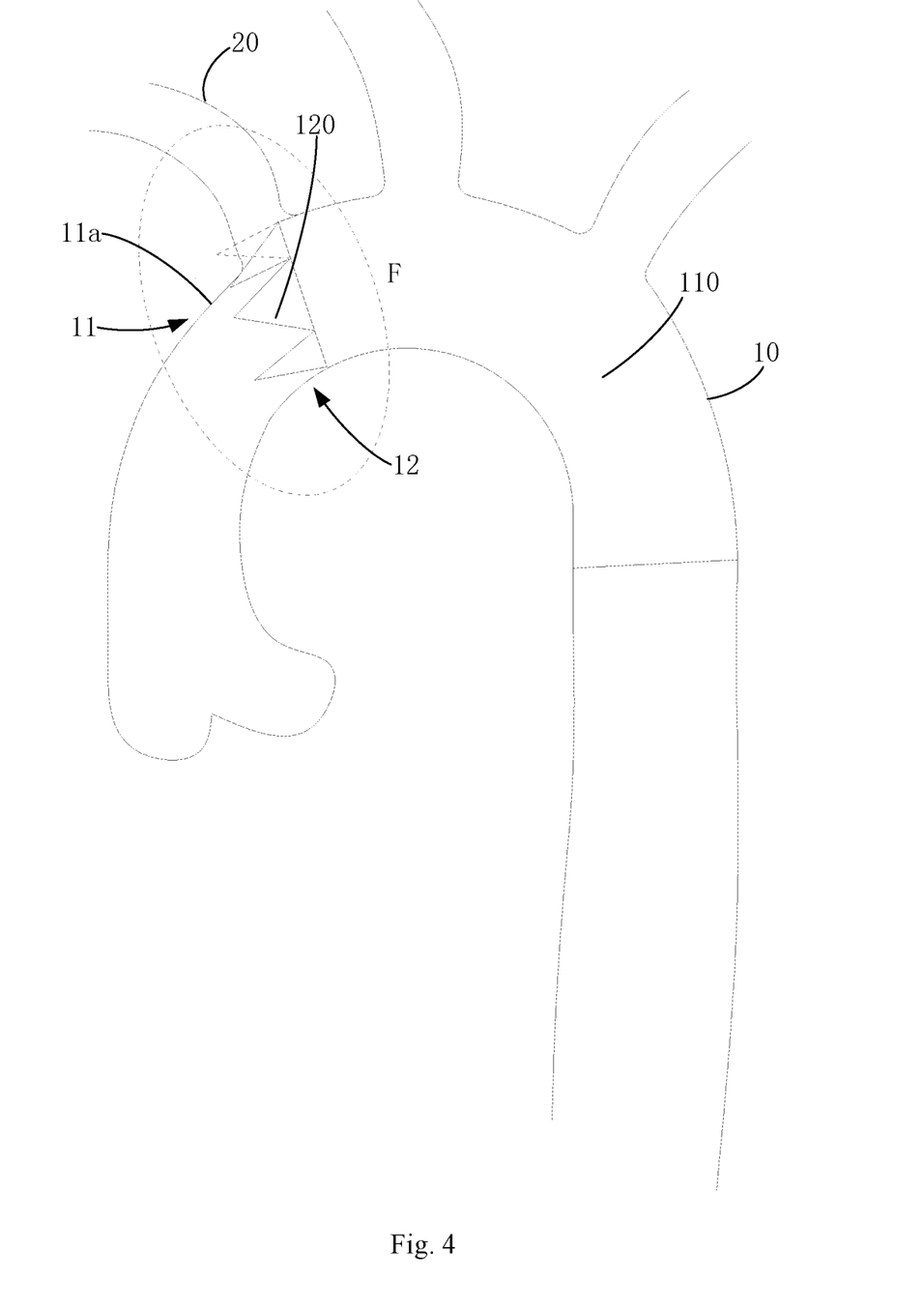
FIG. 4 is a schematic diagram of the covered stent in FIG. 1 being implanted into an arterial vessel.
Figure 5:
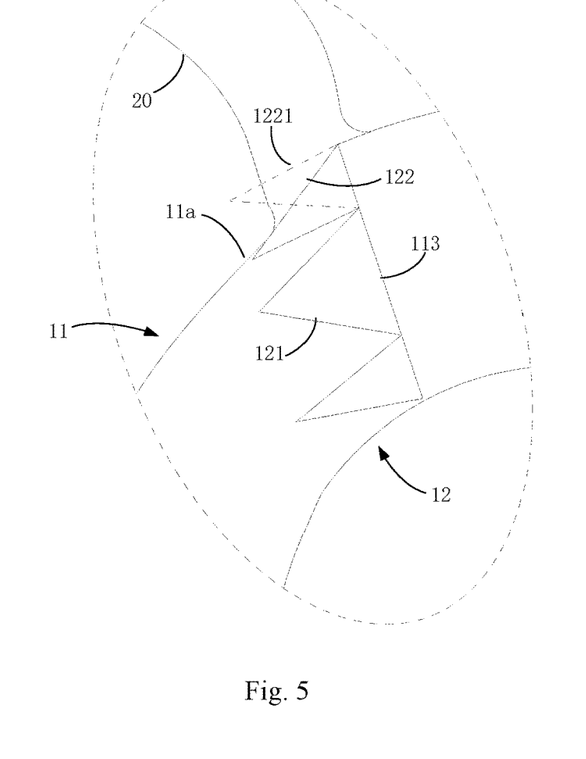
FIG. 5 is a schematic diagram of the enlarged structure at the area F in FIG. 4.

The arterial vessel 10 is curved and has a large curved side 11 and a small curved side 12, and a branch vessel 20 is connected to the large curved side 11 of the arterial vessel 10. After the covered stent 100 is implanted in the arterial vessel 10, the inward-tilting wave body 122 is mounted at the large curved side 11 of the arterial vessel 10. Since the inward-tilting wave body 122 tilts at the set angle α toward the central axis 102 of the covered unit 110, the inward-tilting wave body 122 maintains its original shape without bending, so that at least the following beneficial effects can be achieved:

First, during the anchoring process of the covered stent 100, compared with the case where the inward-tilting wave body 122 does not tilt, the inward-tilting wave body 122 of the present disclosure forms a certain avoidance space due to the tilting, so that the inward-tilting wave body 122 naturally follows the curvature of the large curved side 11 of the arterial vessel 10, which avoids stimulation and compression on the branch vessel 20 and prevents the branch vessel 20 from being directly punctured to cause dissection symptoms.

Figure 6:
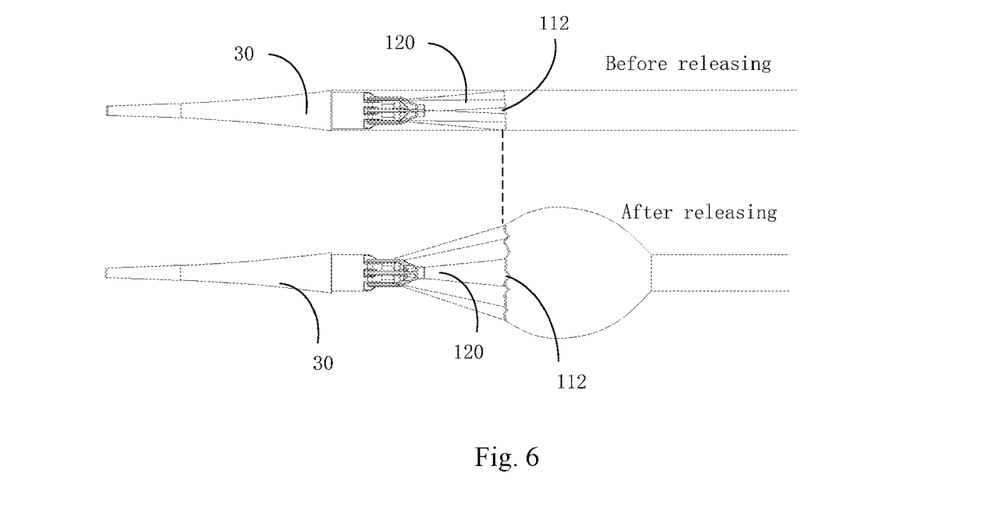
FIG. 6 is a schematic diagram of a comparison before and after the release of the covered stent in FIG. 1.
Figure 7:
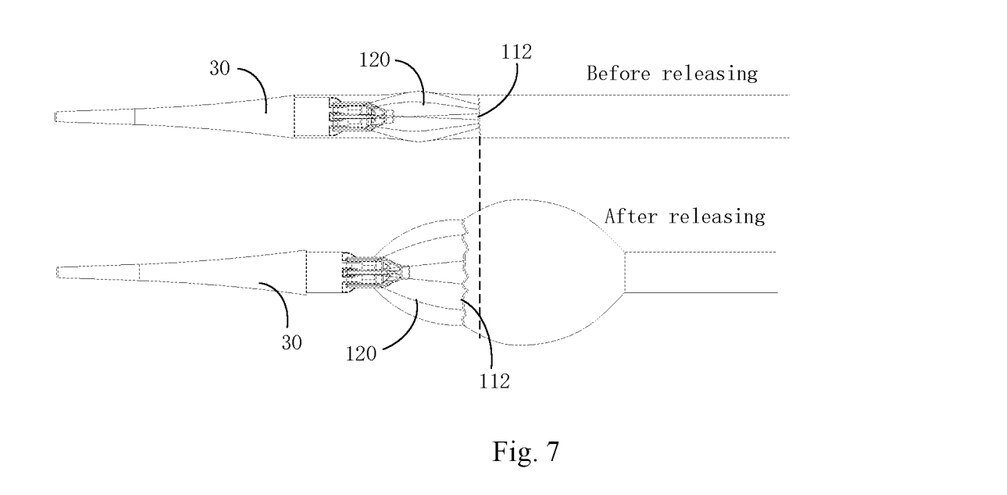
FIG. 7 is a schematic diagram of a comparison before and after the release of a traditional covered stent.

Second, referring to FIGS. 6 and 7, compared with the situation where the top of the traditional inward-tilting wave body 122 bends relative to the root, the inward-tilting wave body 122 of the present disclosure itself does not bend, thereby reducing the difficulty in mounting the entire covered stent 100 into a sheath 30. This also avoids the situation that the inward-tilting wave body 122 hangs on the sheath 30 and is difficult to release during the releasing process. Meanwhile, referring to FIG. 7, the inward-tilting wave body of the traditional covered stent bends. For the end 112 of the covered stent 110 close to the bare unit 120, a position of the end portion 112 after release is shifted to a direction close to the bare unit 120 from the position before release, i.e. shifted to the left, which affects the positioning and anchoring of the covered stent after release; in addition, the bare unit 120 that is inside the sheath 30 is curved and prone to abutment against an inner wall of the sheath 30, thus is difficult to release, which even causes local bulging of the sheath 30 to affect the outer diameter of the sheath 30. Referring to FIG. 6, in the present disclosure, the position of the end portion 112 of the covered unit 110 connected to the bare unit 120 remains constant before and after release, so that the covered stent 100 can be well positioned and anchored; and the bare unit 120 in the sheath 30 is planar, which effectively avoids local bulging of the sheath 30.

Referring to FIGS. 1 to 6, the covered stent 100 according to the first embodiment of the present disclosure includes a bare unit 120 and a covered unit 110, the bare unit 120 includes an upright wave body 121 and an inward-tilting wave body 122 sequentially connected end to end, with both the upright wave body 121 and the inward-tilting wave body 122 made of metal wires, and the two together form a wave ring 101 of the bare unit 120. The covered unit 110 includes a membrane (not shown) and a wave ring (not shown), and the membrane is attached to the wave ring. In short, there is no membrane attached to the wave ring 101 of the bare unit 120, but a membrane is attached to the wave ring of the covered unit 110. With reference to a cylindrical curved surface 111 (infinite extending) where an outer peripheral surface (finite extending) of the covered unit 110 is located, the upright wave body 121 is located on the cylindrical curved surface 111. In this embodiment, the curved surface 111 where the outer peripheral surface of the covered unit 110 is located is a cylindrical curved surface 111a, and it is apparent that the periphery 113 of the covered unit 110 close to the end portion 112 of the bare unit 120 is circular. The upright wave body 121 includes a second wave crest 121a, a second wave trough 121b and a second wave rod 121c which connects the second wave crest 121a and the second wave trough 121b, a vertex of the second wave trough is located on the periphery 113 of the end portion 112 of the covered unit 110 which is close to the bare unit 120, and the second wave crest 121a is further from the covered unit 110 than the second wave trough 121b. The inward-tilting wave body 122 tilts (tilts inward) at a set angle α toward a direction close to the central axis 102 of the covered unit 110 relative to the cylindrical curved surface 111a, and from the first wave crest 122a to the first wave trough 122b, the radial distance e from the inward-tilting wave body 122 to the central axis 102 of the covered unit 110 increases linearly; and the inward-tilting wave body 122 itself does not bend. The upright wave body 121 is located on the cylindrical curved surface 111a. Obviously, from the second wave crest 121a to the second wave trough 121b of the upright wave body 121, the radial distance E from the upright wave body 121 to the central axis 102 of the covered unit 110 is equal throughout. Obviously, the vertical projection of the upright wave body 121 on the covered unit 110 falls entirely on the periphery 113, and the vertical projection of the inward-tilting wave body 122 on the covered unit 110 falls within a contour of the periphery 113.

It should be noted that the curved surface 111 where the outer peripheral surface of the covered unit 110 is located may also be in other shapes, such as a truncated cone shape, in which situation the angle between the upright wave body 121 and the central axis of the covered unit 110 is equal to the angle between a generatrix of the covered unit 110 and the central axis of the covered unit 110.

Figure 2:
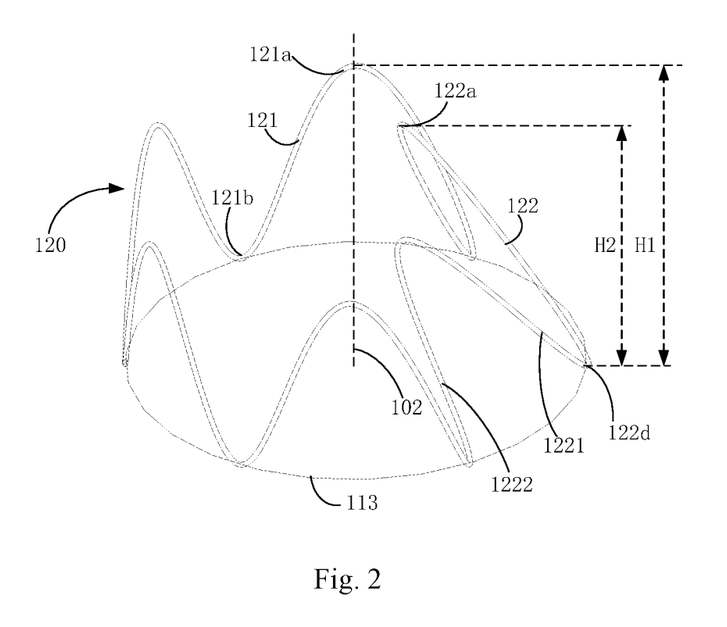
FIG. 2 is a schematic diagram of a partial structure of FIG. 1 after a covered unit is removed.
Figure 3:
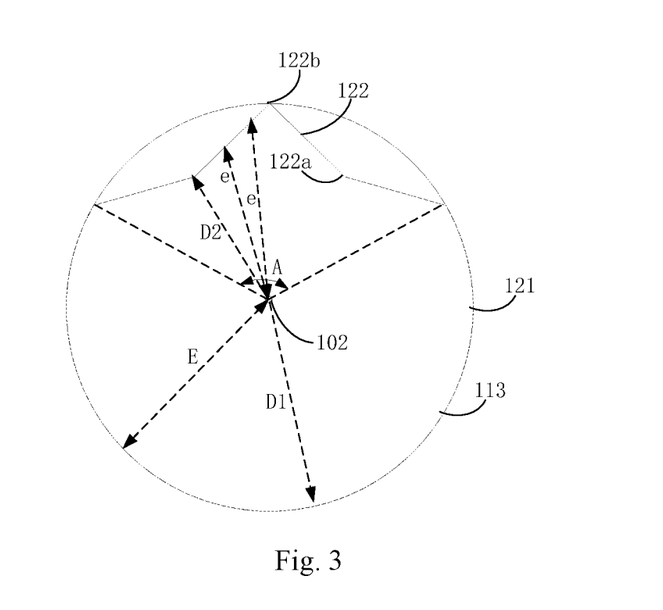
FIG. 3 is a schematic top view of FIG. 1.

The number of the inward-tilting wave bodies 122 is at least two, for example, two to four. All the inward-tilting wave bodies 122 are continuously arranged on the periphery 113 of the end portion 112 of the covered unit 110 close to the bare unit 120, that is, there is no upright wave body 121 in the two adjacent inward-tilting wave bodies 122 in the middle. All the inward-tilting wave bodies 122 occupy an arc of a certain length on the periphery 113 of the end portion of the covered unit 110 close to the bare unit 120, and the central angle (i.e. the angle of the arc) corresponding to the arc is A, where the value range of A is greater than or equal to 60° and less than or equal to 180°; for example, the value of A is 65°, 70°, 75°, 80°, 85°, 90°, 95°, 110°, 120° or 150° etc. Therefore, the anchoring force of the bare unit 120 is prevented from decreasing due to having too many inward-tilting wave bodies 122 or too large a value; a sufficient number of upright wave bodies 121 can effectively support the entire covered stent 100, and the covered stent 100 can be accurately released.

The distance from a vertex of the second wave crest 121a to a plane where the periphery 113 of the end portion 112 of the covered unit 110 close to the bare unit 120 is located is $H_1$, where $H_1$ is greater than or equal to 5 mm and less than or equal to 25 mm; and the distance from a vertex of the first wave crest 122a to the plane where the periphery 113 of the end portion of the covered unit 110 close to the bare unit 120 is located is $H_2$, where $H_2/H_1$ is greater than or equal to 0.5 and less than or equal to 0.95; for example, the value of $H_2/H_1$ is 0.6, 0.7, 0.8, 0.85 or 0.9 etc. Since $H_2$ is smaller than the value of $H_1$ and the difference between the two is not large, the probability for the inward-tilting wave body 122 puncturing the branch vessel 20 is reduced, and the stability of release for the covered stent 100 and the uniformity of the radial supporting force can be ensured.

The radius of the circular curve where the second wave crest 121a is located is r, and the radius of the circular curve where the first wave crest 122a is located is R, where $0.8 \text{ mm} \leq R \leq 3 \text{ mm}$, $1.5 \text{ mm} \leq r \leq R \leq 2.5 \text{ mm}$, and the value of R can be greater than the value of r. For the radius R of the circular curve where the first wave crest 122a is located, the value of R cannot be too large or too small; if the value of R is too small, it may affect the fatigue strength of the bare unit 120, and may also cause the wave crest of the inward-tilting wave body 122 to be too sharp to increase the risk of puncturing the branch vessel 20; in addition, if the value of R is too large, this increases the difficulty in mounting the covered stent 100 into the sheath 30, and even a sheath 30 with larger outer diameter is required to mount the covered stent 100, which may affect the delivery of the sheath 30 in the blood vessel.

Since both the vertex of the first wave trough 122b and the vertex of the second wave trough 121b are both located on the periphery 113 of the end portion 112 of the covered unit 110 close to the bare unit 120, when the radius of the periphery 113 of the end portion 112 of the covered unit 110 close to the bare unit 120 is $D_1$, it is apparent that the radial distances from the vertex of the first wave trough 122b and the vertex of the second wave trough 121b to the central axis 102 of the covered unit 110 are also $D_1$, where the value of $D_1$ can be 18 to 50 mm. The radial distance from the vertex 122a of the first wave crest to the central axis 102 is $D_2$, where $D_2/D_1$ is greater than or equal to 0.5 and less than or equal to 0.95. For example, the value of $D_2/D_1$ may be 0.55, 0.6, 0.75 or 0.9. The value of $D_2$ cannot be too large or too small. When the value of $D_2$ is too small, the inward angle α of the inward-tilting wave body 122 is relatively large, which causes the resilience force of the bare unit 120 to be small, so that the phenomenon that the bare unit 120 cannot be ejected out of the sheath 30 easily occurs to affect the release of the bare unit 120, and even the release of the bare unit 120 might fail due to the fact that the bare unit 120 cannot be ejected out. In addition, the implanted inward-tilting wave body 122 cannot be anchored to the inner wall of the arterial vessel 10; i.e. the inward-tilting wave body 122 is suspended in the arterial vessel 10, which increases the risk of thrombus formation and causes the anchoring force of the bare unit 120 to be insufficient. When the value of $D_2$ is too large, the inward-tilting wave body 122 tilts inward a small angle α, which is difficult to reduce the risk that the wave crest of the inward-tilting wave body 122 penetrates into the branch vessel 20.

The first wave rod 122c includes a first connecting segment 1221 and a second connecting segment 1222 connected at the first wave crest 122a, the first wave trough 122b close to the first connecting segment 1221 is mounted close to the large curved side 11 of the arterial vessel 10, and the length of the first connecting segment 1221 on at least one inward-tilting wave body 122 is greater than that of the second connecting segment 1222. Of course, when the number of the inward-tilting wave bodies 122 is two, the lengths of the two first connecting segments 1221 of the two inward-tilting wave bodies 122 can be both greater than the lengths of the second connecting segments 1222, the first wave troughs 122b close to the two first connecting segments 1221 coincide with each other, and the first wave troughs 122b form a connecting point 122d of the two inward-tilting wave bodies 122; and after the covered stent 100 is implanted, the connecting point 122d is aligned with a center line 11a of the large curved side 11 of the arterial vessel 10, and in the circumferential direction of the arterial vessel 10, the two inward-tilting wave bodies 122 are respectively located on two sides of the center line 11a. Compared with the lengths of the first connecting segments 1221 and the second connecting segments 1222 being equal, when the length of the first connecting segments 1221 is greater than the length of the second connecting segments 1222, the inward-tilting wave body 122 is in a non-axisymmetric shape, so that the gap between the two inward-tilting wave bodies 122 in the circumferential direction of the arterial vessel 10 is increased, which further reduces the probability that the wave crests of the inward-tilting wave bodies 122 penetrate into the branch vessel 20.

The diameter of the metal wire for manufacturing the upright wave body 121 is $d_1$, where $d_1$ is greater than or equal to 0.3 mm and less than or equal to 0.55 mm. The diameter of the metal wire for manufacturing the inward-tilting wave body 122 is $d_2$, where $d_2/d_1$ is greater than or equal to 0.2 and less than or equal to 0.9; for example, the value of $d_2/d_1$ may be 0.3, 0.4, 0.5, 0.6 or 0.8. Accordingly, the wire diameter of the inward-tilting wave body 122 is smaller than that of the upright wave body 121, which will increase the flexibility of the inward-tilting wave body 122 and further reduce the risk that the wave crest of the inward-tilting wave body 122 puncturing the branch vessel 20.

Second Embodiment

Figure 8:
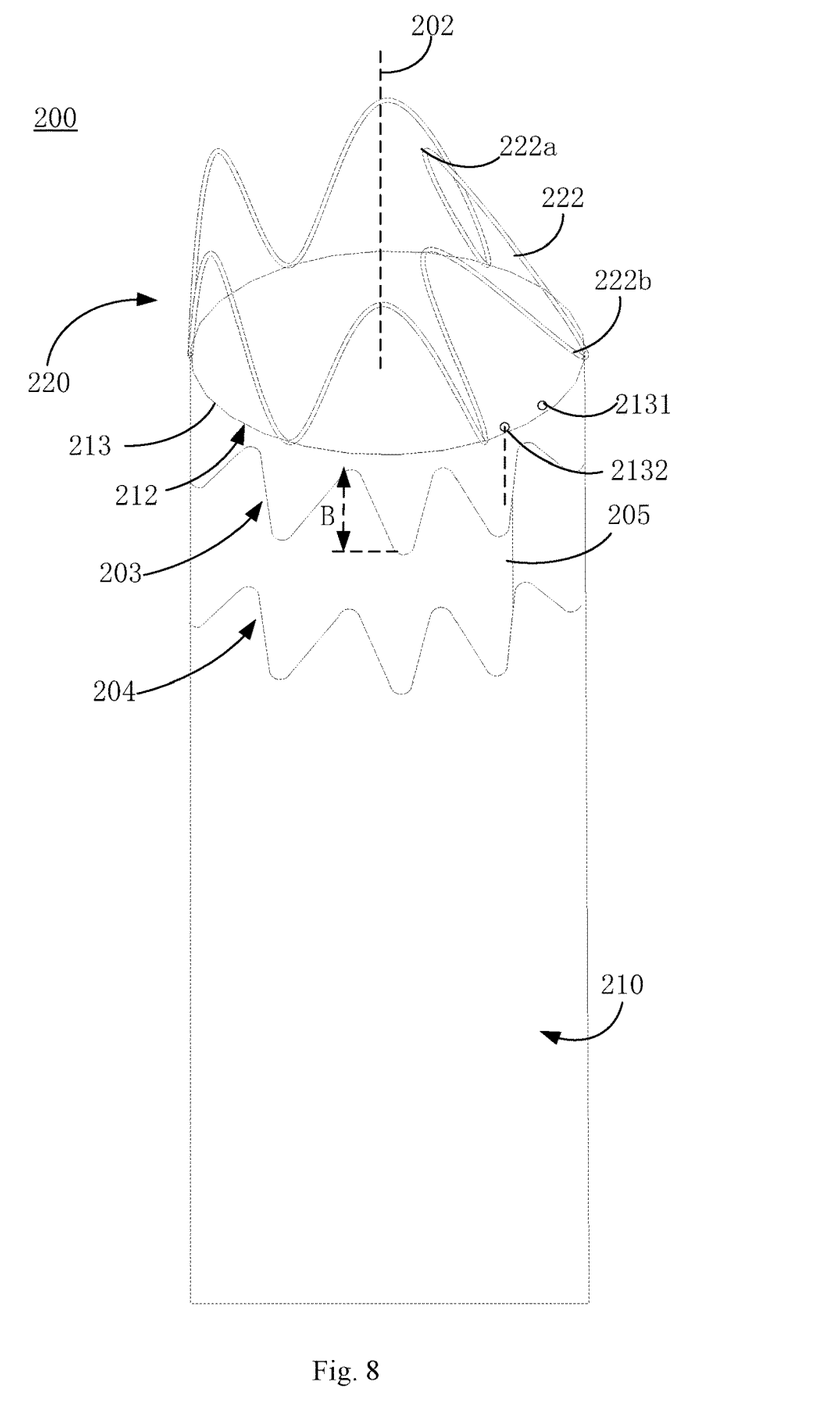
FIG. 8 is a schematic structural diagram of a first example of a covered stent according to a second embodiment.
Figure 9:
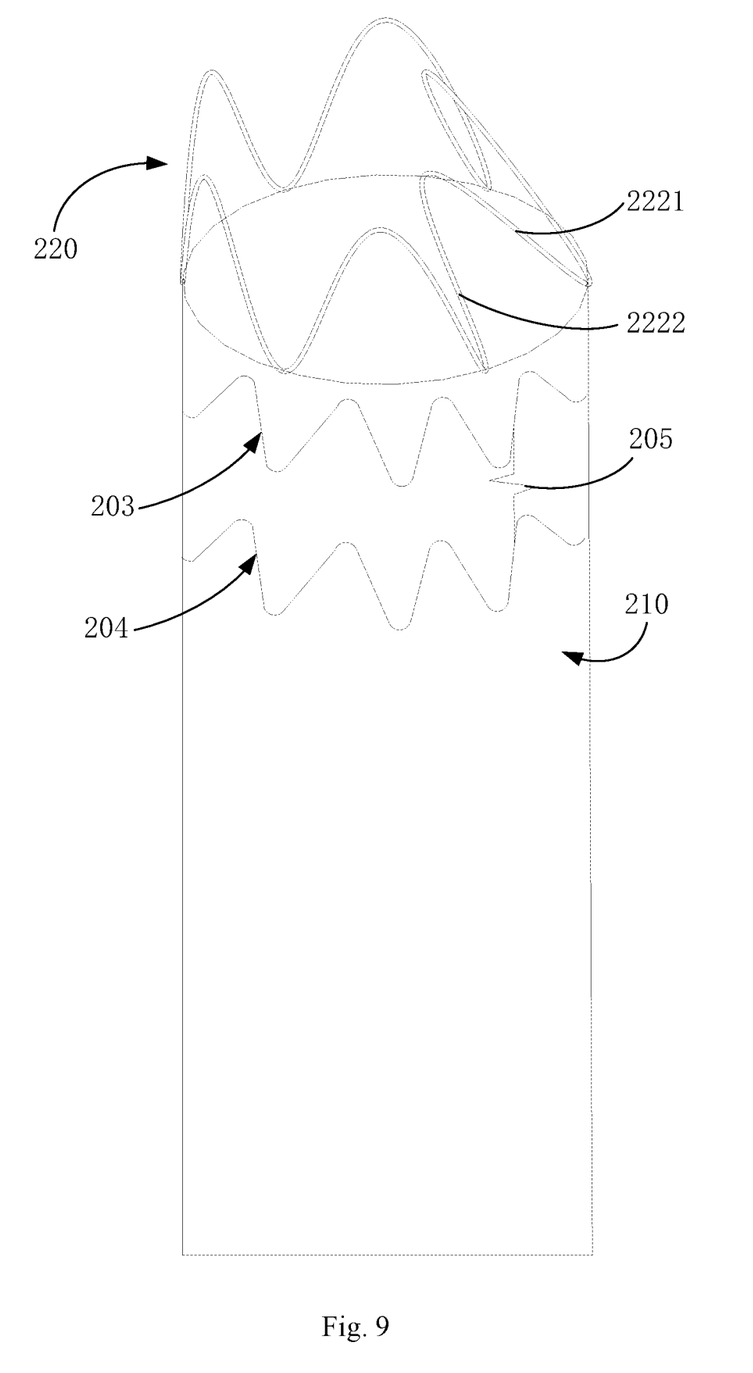
FIG. 9 is a schematic structural diagram of a second example of a covered stent according to the second embodiment.

Referring to FIGS. 8 and 9, the covered stent 200 according to the second embodiment of the present disclosure differs from the first embodiment in that a connector 205 is connected between two wave rings that arranged close to the bare unit 220 of the covered unit 210.

Specifically, the covered unit 210 includes a first wave ring 203, a second wave ring 204 and a connector 205; the connector 205 extends along the central axis 202 of the covered unit 210. The first wave ring 203 is closest to the bare unit 220, and the second wave ring 204 is closest to the first wave ring 203 relative to other wave rings. One of the inward-tilting wave bodies 222 occupies a circular arc on the periphery 213 of the end portion 212 of the covered unit 210 close to the bare unit 220, and the arc has a midpoint 2131 that circumferentially bisects the arc. Of course, when the inward-tilting wave body 222 is in an axisymmetric shape (i.e. the length of the first connecting segment 2221 of the inward-tilting wave body 222 is equal to the length of the second connecting segment 2222), the midpoint 2131 is just an intersection point of the symmetry axis of the inward-tilting wave body 222 and the periphery 213 of the end portion of the covered unit 210 close to the bare unit 220, and the symmetry axis passes through the vertex of the first wave crest 222a and the intersection point. The extension line of the connector 205 has an intersection point 2132 with the periphery 213 of the end portion of the covered unit 210 close to the bare unit 220, and the center angle of a minor arc between the intersection point 2132 and the midpoint 2131 on the periphery 213 of the end portion of the covered unit 210 close to the bare unit 220 is less than or equal to 120°.

By providing the connector 205 and causing the center angle of the minor arc between the intersection point 2132 and the midpoint 2131 on the periphery 213 of the end portion of the covered unit 210 close to the bare unit 220 to be less than or equal to 120°, a good axial supporting effect can be provided for the first wave ring 203. After the covered stent 200 is implanted, the first wave ring 203 is prevented from moving close to the second wave ring 204 to produce axial contraction, so that the phenomenon of warping or "beak" occurring at a proximal end of the covered stent 200 is avoided, the wave crest of the inward-tilting wave body 222 is prevented from penetrating into the branch vessel 20 (see FIG. 4), the phenomenon of inner leakage caused by the entry of blood into the aneurysm through the "beak" can also be effectively avoided, and the isolation performance of the covered stent 200 is ensured. The proximal end of the covered stent 200 refers to the end closer to the heart after implantation; i.e., the end where the bare unit 220 is located. The so-called "beak" refers to the proximal end of the covered stent 200 not being completely attached to the inner wall of the arterial vessel 10 because it cannot adapt to the curvature of the arterial vessel 10, so that there is an angle between the proximal end of the covered stent 200 and the inner wall of the arterial vessel 10 (i.e. a wedge-shaped gap), and the wedge-shaped gap is visually called a "beak".

The connector 205 is connected between a wave trough of the first wave ring 203 and a wave crest of the second wave ring 204, and an axial projection distance from a vertex of a wave crest of the first wave ring 203 to a vertex of the wave trough thereof is B; if the value of B is too small, the covered unit 210 cannot be anchored and sealed; and if the value of B is too large, the flexibility of the entire covered stent 200 to the curvature of the arterial vessel 10 will be affected. The axial length of the connector 205 is b, where b is greater than or equal to 5 mm and less than or equal to 20 mm, and b/B is greater than or equal to 0.3 and less than or equal to 1; for example, the value of b/B is 0.3, 0.5, 0.6 or 1, etc. The value of b/B cannot be too small or too large; when the value of b/B is too small, the flexibility of the covered stent 200 is low; and when the value of b/B is too large, the continuity and radial support of the covered stent 200 are poor.

The number of the connectors 205 may be two, and in the circumferential direction of the covered unit 210, the central angle corresponding to the circumferential distance between the two connectors 205 is less than or equal to 180°. After the covered stent 200 is implanted into the arterial vessel 10, in the circumferential direction of the arterial vessel 10, the two connectors 205 are symmetrically distributed along the centerline 11a of the large curved side 11 of the arterial vessel 10; that is, the circumferential distances from the two connectors 205 to the centerline 11a of the large curved side 11 of the arterial vessel 10 are equal, so that the central angle corresponding to the circumferential distance between each connector 205 and the center line 11a of the large curved side 11 of the arterial vessel 10 is less than or equal to 90°. In this way, the phenomenon of warping or "beak" can be further avoided.

The connector 205 may be rod-shaped, that is, the connector is a connecting rod. The connecting rod may be linear. Of course, two ends of the connecting rod are linear, and a middle part of the connecting rod can be curved to a certain extent, so that the connector 205 enables the entire covered stent 200 to have certain compliance on the basis of forming an axial support.

Third Embodiment

Figure 10:
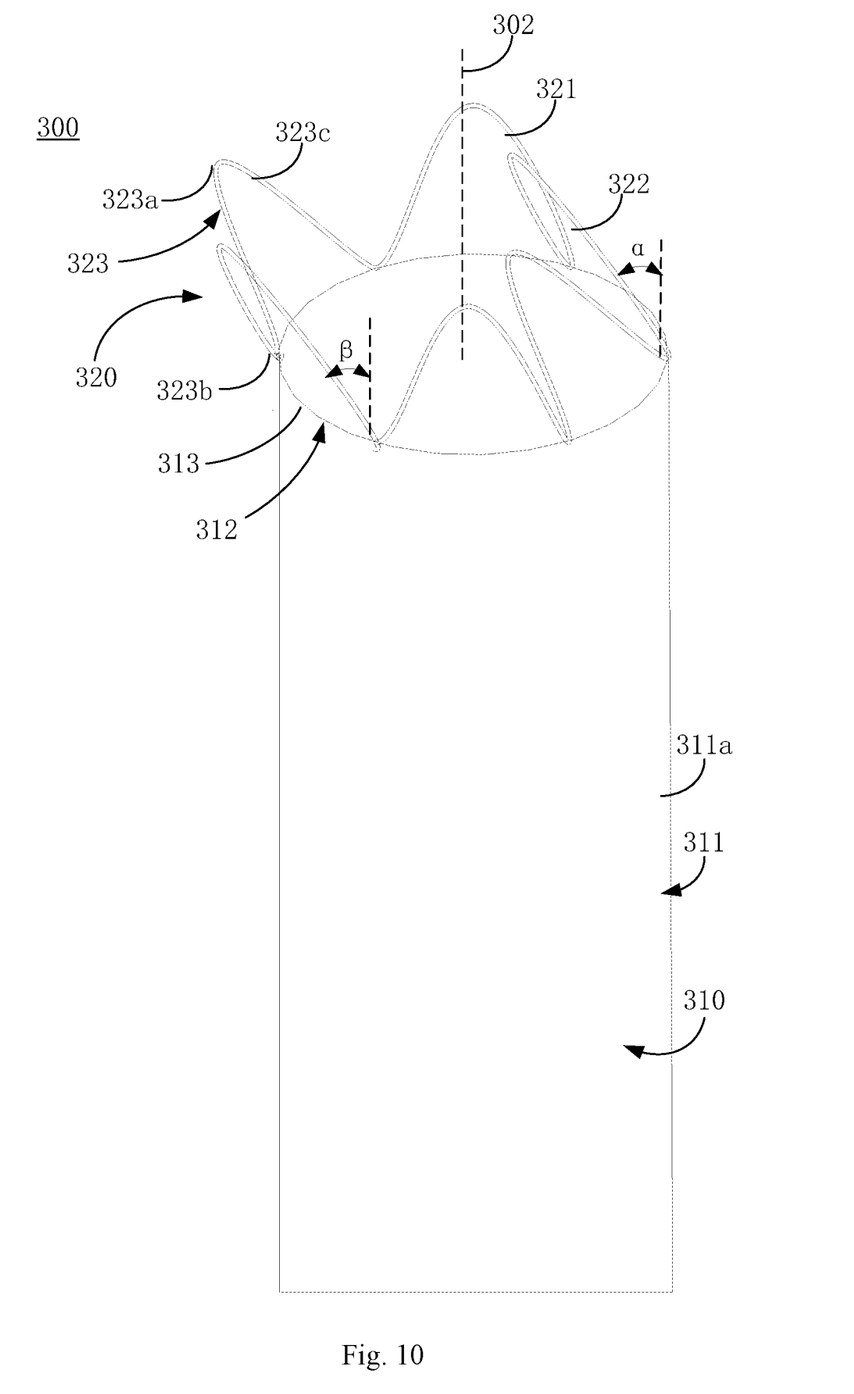
FIG. 10 is a schematic structural diagram of a covered stent according to a third embodiment.
Figure 11:
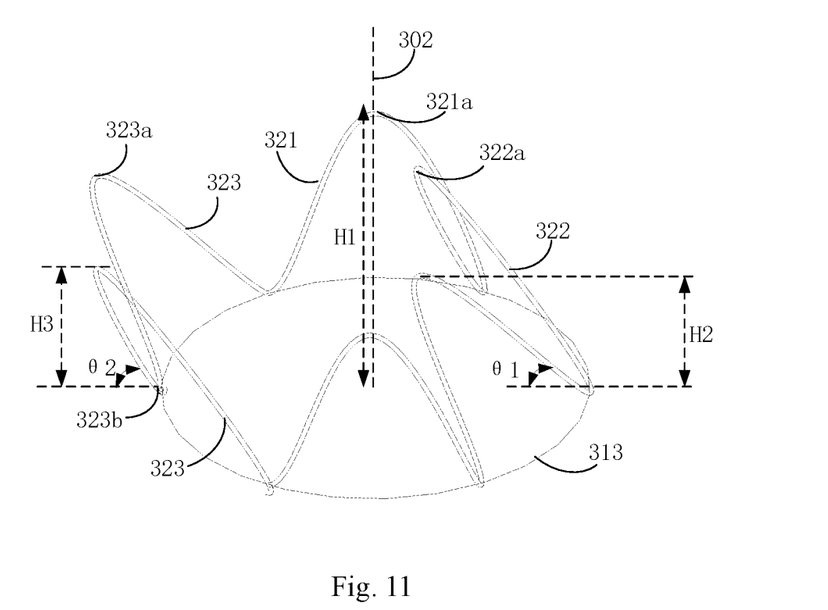
FIG. 11 is a schematic diagram of a partial structure of FIG. 10 after a covered unit is removed.
Figure 12:
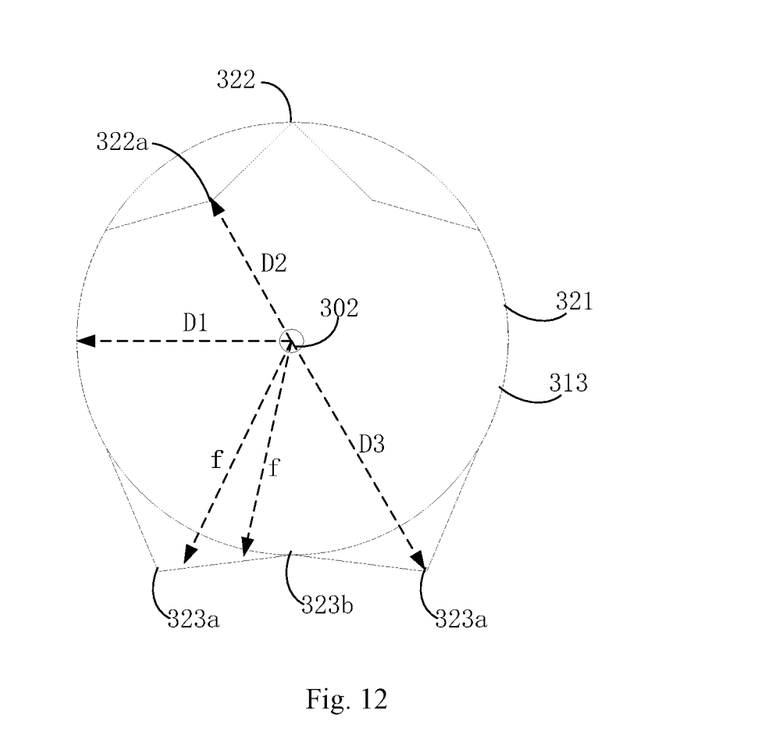
FIG. 12 is a schematic top view of FIG. 10.

Referring to FIGS. 10 to 12, the covered stent 300 according to the third embodiment of the present disclosure differs from the first embodiment in that the bare unit 320 further includes an outward-tilting wave body 323.

The outward-tilting wave body 323 is connected to the upright wave body 321 and arranged on a periphery 313 of an end portion 312 of the covered unit 310 close to the bare unit 320, and the outward-tilting wave body 323 tilts (tilts outwardly) at a set angle β from the curved surface 311 towards a direction away from the central axis 302 of the covered unit 310. The outward-tilting wave body 323 is mounted on the small curved side 12 of the arterial vessel 10 (see FIG. 4); i.e., the outward-tilting wave body 323 is arranged opposite of the inward-tilting wave body 322 mounted on the large curved side 11 of the arterial vessel 10. Since the outward-tilting wave body 323 tilts outwardly at the set angle β, the outward-tilting wave body 323 can well adapt to the curvature of the small curved side 12 of the arterial vessel 10, ensuring that the outward-tilting wave body 323 is tightly attached to the inner wall surface of the small curved side 12 of the arterial vessel 10, so that the anchoring effect of the bare unit 320 is improved. Meanwhile, the phenomenon of "beak" between the proximal end of the covered stent 300 and the arterial vessel 10 can be effectively avoided, and the risk of inner leakage of the covered stent 300 is further reduced.

Specifically, the curved surface 311 where the outer circumferential surface of the covered unit 310 is also a cylindrical curved surface 311a; the outward-tilting wave body 323 also includes a third wave crest 323a, a third wave trough 323b, and a third wave rod 323c for connecting the third wave crest 323a with the third wave trough 323b; a vertex of the third wave trough 323b is located on the periphery 313 of the end portion 312 of the covered unit 310 close to the bare unit 320, the third wave crest 323a is further from the covered unit 310 than the third wave trough 323b, the third wave rod 323 is planar, and the outward-tilting wave body 323 itself does not bend; and after the outward-tilting wave body 323 tilts outwardly at the set angle β from the third wave crest 323a to the third wave trough 323b, the radial distance f from the outward-tilting wave body 323 to the central axis 302 of the covered unit 310 gradually decreases. In short, the shapes of the outward-tilting wave body 323 and the inward-tilting wave body 322 can be exactly the same except that they tilt in different directions relative to the cylindrical curved surface 311a; i.e. the inward-tilting wave body 322 tilts inwardly to adapt to the curvature of the large curved side 11 of the arterial vessel 10; and the outward-tilting wave body 323 tilts outwardly to adapt to the curvature of the small curved side 12 of the arterial vessel 10.

The angles θ1 formed by the inward-tilting wave body 322 and the plane where the periphery of the end portion of the covered unit 310 close to the bare unit 320 is equal to the angles θ2 formed by the outward-tilting wave body 323 and the plane where the periphery of the end portion of the covered unit 310 is close to the bare unit 320. In other words, the tilting angles α and β of the inward-tilting wave body 322 and the outward-tilting wave body 323 with respect to the cylindrical curved surface 311a are equal, while the tilting directions are opposite. According to the degree of curvature of the arterial vessel 10, in order to avoid the situation where the inward-tilting wave body 322 punctures into the branch vessel 20 or the resulting phenomenon of "beak", and to avoid the phenomenon of "beak" caused by the outward-tilting wave body 323, the values of the angles θ1 and θ2 are between 60° and 85°. For example, the values of the angles θ1 and θ2 may be 60°, 65°, 70°, 75°, 80° or 85° etc. When the angles θ1 and θ2 are equal, the bare unit 320 can be formed by one processing step, which omits the intermediate clamping step and conversion time and greatly simplifies the manufacturing process of the entire bare unit 320, thereby reducing the manufacturing cost of the entire covered stent 300.

The distance from the vertex of the second wave crest 321a to the plane where the periphery 313 of the end portion 312 of the covered unit 310 close to the bare unit 320 is located is $H_1$, the distance from the vertex of the first wave crest 322a to the plane where the periphery 313 of the end portion 312 of the covered unit 310 close to the bare unit 320 is located is $H_2$, and the distance from the vertex of the third wave crest 323a to the plane where the periphery 313 of the end portion 312 of the covered unit 310 close to the bare unit 320 is located is $H_3$, where $H_2/H_3$ is greater than or equal to 0.8 and less than or equal to 1.2. In one embodiment, $H_2=H_3$, and the value of $H_3/H_1$ is equal to the value of $H_2/H_1$; i.e. the value of $H_3/H_1$ can be 0.6, 0.7, 0.8 or 0.9, which can also simplify the manufacturing process of the bare unit 320.

The radius of the periphery 313 of the end portion 312 of the covered unit 310 close to the bare unit 320 is $D_1$, the radial distance from the vertex of the first wave crest 322a to the central axis 302 is $D_2$, and the radial distance from the vertex of the third wave crest 323a to the central axis 302 is $D_3$, where $D_3 > D_1 > D_2$; and $D_3 - D_1 = D_1 - D_2$. At this time, when the entire covered stent 300 is subjected to an axial impact force, the directions of elastic reaction forces generated by both the inward-tilting wave body 322 and the outward-tilting wave body 323 are the same, which helps to ensure the stability of release of the entire covered stent 300.

Fourth Embodiment

Figure 13:
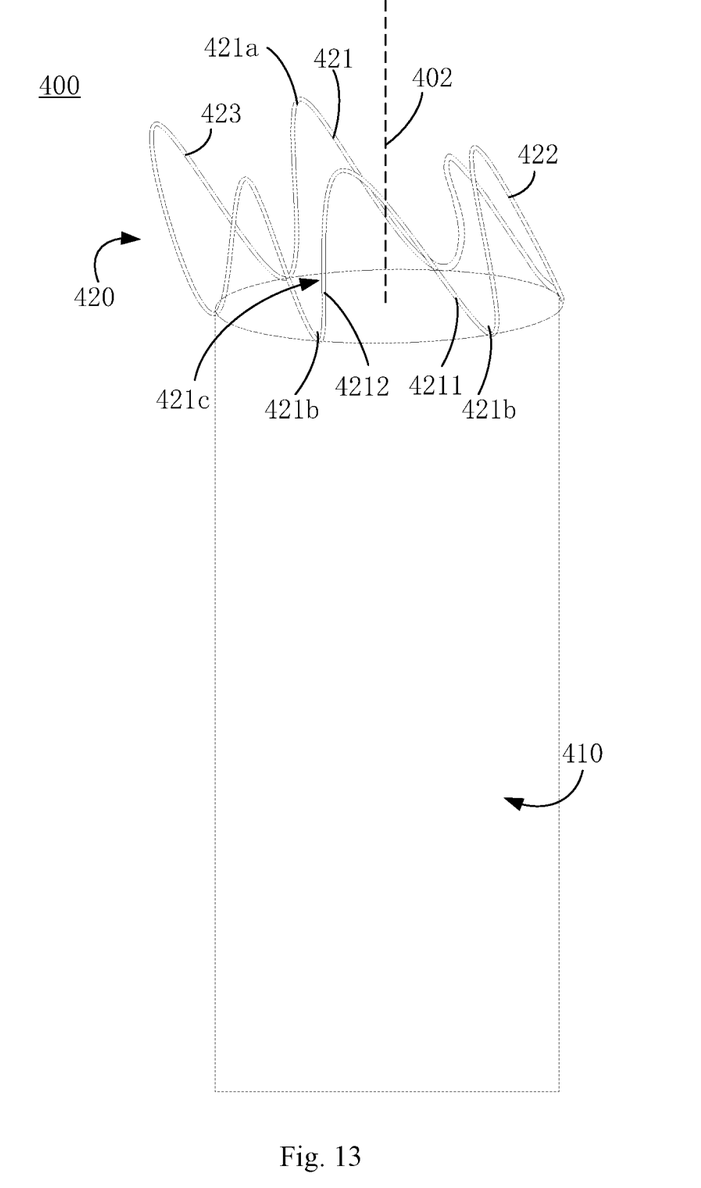
FIG. 13 is a schematic structural diagram of a covered stent according to a fourth embodiment.

Referring to FIG. 13, the covered stent 400 according to the fourth embodiment of the present disclosure differs from the third embodiment in that the upright wave body 421 is in an asymmetric shape.

Specifically, the second wave rod 421c includes a third connecting segment 4211 and a fourth connecting segment 4212 which are both connected at the second wave crest 421a. In the circumferential direction of the covered stent 400, the vertex of the second wave trough 421b close to the third connecting segment 4211 is close to the inward-tilting wave body 422, the vertex of the second wave trough 421b close to the fourth connecting segment 4212 is away from the inward-tilting wave body 422 (i.e., close to the outward-tilting wave body 423), and the length of the third connecting segment 4211 is greater than that of the fourth connecting segment 4212.

Compared with the case where the length of the third connecting segment 4211 is equal to that of the fourth connecting segment 4212, since the length of the third connecting segment 4211 is greater than that of the fourth connecting segment 4212, and the entire upright wave body 421 is in a non-axisymmetric shape, the second wave crest 421a of the upright wave body 421 is shifted in a direction away from the inward-tilting wave body 422, i.e., shifted to the left. Referring to FIG. 11, there are two-second wave crests on left and right sides of the central axis 402 of the covered unit 410. Referring to FIG. 13, since the second wave crests 421a are shifted to the left relatively, there are four-second wave crests on the left side of the central axis 402 of the covered unit 410 and two-second wave crests on the right side of the central axis 402 of the covered unit 410. Therefore, when the covered stent 400 is released in the arterial vessel 10 and a circumferential deviation occurs (within a range of)±90°, the upright wave body 421 close to the large curved side 11 of the arterial vessel 10 still does not puncture the branch vessel 20 due to the mounting deviation, which further avoids the puncture of the branch vessel 20 by the bare unit 420.

The technical features of the above-described embodiments may be combined arbitrarily. For the purpose of simplicity in description, all the possible combinations of the technical features in the above embodiments are not described. However, as long as the combinations of these technical features do not have contradictions, they shall fall within the scope of the specification.

The foregoing embodiments only describe several implementation modes of the present disclosure, and their descriptions are specific and detailed, but cannot therefore be understood as limitations to the patent scope of the present disclosure. It should be noted that a person of ordinary skill in the art could also make many alterations and improvements without departing from the spirit of the present disclosure, and these alterations and improvements shall all fall within the protection scope of the present disclosure. Therefore, the protection scope of the present disclosure shall be in accordance with the appended claims.

The invention claimed is:

1. A covered stent, wherein the covered stent comprises: a covered unit; and
a bare unit, which is a ring-shaped structure and arranged on a periphery of an end portion of the covered unit, wherein the bare unit comprises an inward-tilting wave body comprising a first wave crest and a first wave rod, with the first wave rod connected to the first wave crest, the first wave crest is further from the covered unit than other positions of the inward-tilting wave body, the first wave rod is planar and is inclined at an angle with respect to a central axis of
the periphery of the end portion of the covered unit, and from the first wave crest to an end of the bare unit adjacent to the covered unit a radial distance from the inward-tilting wave body to the central axis of the periphery of the covered unit gradually increases; and
wherein the bare unit comprises at least two inward-tilting wave bodies, all of the inward-tilting wave bodies are continuously arranged on the periphery of the end portion of the covered unit, and angles of circular arcs occupied by all of the inward-tilting wave bodies on the periphery of the end portion of the covered unit close to the bare unit are A, where A is more than or equal to 60° and less than or equal to 180°.

2. The covered stent according to claim 1, wherein each inward-tilting wave body further comprises a first wave trough, a vertex of the first wave trough is located on the periphery of the end portion of the covered unit, and a respective first wave rod connects a respective first wave crest with a respective first wave trough.

3. A covered stent, wherein the covered stent comprises:
a covered unit; and
a bare unit, which is a ring-shaped structure and arranged on a periphery of an end portion of the covered unit, wherein the bare unit comprises an inward-tilting wave body comprising a first wave crest and a first wave rod, with the first wave rod connected to the first wave crest, the first wave crest is further from the covered unit than other positions of the inward-tilting wave body, the first wave rod is planar, and from the first wave crest to an end of the bare unit adjacent to the covered unit a radial distance from the inward-tilting wave body to a central axis of the covered unit gradually increases;
wherein the covered unit comprises a first wave ring, a second wave ring and a connector, the first wave ring is relatively closest to the bare unit, and the connector extends parallel to the central axis and is connected between the first wave ring and the second wave ring; an extension line of the connector has an intersection point with the periphery of the end portion of the covered unit, the inward-tilting wave body, which occupies a circular arc on the periphery of the end portion of the covered unit close to the bare unit, has a midpoint that circumferentially bisects the arc, and a center angle of a minor arc between the intersection point and the midpoint on the periphery of the end portion of the covered unit close to the bare unit is less than or equal to 120°.

4. The covered stent according to claim 3, wherein the connector is connected between a wave trough of the first wave ring and a wave crest of the second wave ring, an axial distance from a vertex of a wave crest of the first wave ring to a vertex of the wave trough thereof is B, and an axial length of the connector is b, where b/B is more than or equal to 0.3 and less than or equal to 1.

5. The covered stent according to claim 3, wherein the covered unit comprises two connectors, and in a circumferential direction of the covered unit, a central angle corresponding to a circumferential distance between the two connectors is less than or equal to 180°.

6. A covered stent, wherein the covered stent comprises:
a covered unit; and
a bare unit, which is a ring-shaped structure and arranged on a periphery of an end portion of the covered unit, wherein the bare unit comprises an inward-tilting wave body comprising a first wave crest and a first wave rod, with the first wave rod connected to the first wave crest, the first wave crest is further from the covered unit than other positions of the inward-tilting wave body, the first wave rod is planar, and from the first wave crest to an end of the bare unit adjacent to the covered unit a radial distance from the inward-tilting wave body to a central axis of the covered unit gradually increases;
wherein the inward-tilting wave body further comprises a first wave trough, a vertex of the first wave trough is located on the periphery of the end portion of the covered unit and the first wave rod connects the first wave crest with the first wave trough;
wherein the bare unit further comprises an upright wave body connected to the inward-tilting wave body, and with reference to a cylindrical curved surface where an outer circumferential surface of the covered unit is located, the upright wave body is located on the cylindrical curved surface.

7. The covered stent according to claim 6, wherein the upright wave body comprises a second wave crest and a second wave trough, the second wave crest is further from the covered unit than the second wave trough, a distance between a vertex of the second wave crest and a plane where the periphery of the end portion of the covered unit close to the bare unit is $H_1$, and a distance from a vertex of the first wave crest to the plane where the periphery of the end portion of the covered unit close to the bare unit is located is $H_2$, where $H_2/H_1$ is more than or equal to 0.5 and less than or equal to 0.95.

8. The covered stent according to claim 7, wherein a radius of the periphery of the end portion of the covered unit close to the bare unit is $D_1$, and a radial distance between the vertex of the first wave crest and the central axis is $D_2$, where $D_2/D_1$ is more than or equal to 0.5 and less than or equal to 0.95.

9. The covered stent according to claim 7, wherein the first wave rod defines a first connecting segment, and wherein a second connecting segment is connected at the first wave crest, the vertex of the first wave trough is configured to be mounted close to a large curved side of an arterial vessel.

10. The covered stent according to claim 7, wherein the bare unit further comprises an outward-tilting wave body connected to the upright wave body and arranged on the periphery of the end portion of the covered unit; the outward-tilting wave body comprises a third wave crest, a third wave trough, and a third wave rod for connecting the third wave crest with the third wave trough; a vertex of the third wave trough is located on the periphery of the end portion of the covered unit, the third wave crest is further from the covered unit than the third wave trough, the third wave rod is planar, and from the third wave crest to the third wave trough, a radial distance from the outward-tilting wave body to the central axis of the covered unit gradually decreases.

11. The covered stent according to claim 10, wherein an angle between the inward-tilting wave body and a plane where the periphery of the end portion of the covered unit is located is equal to an angle between the outward-tilting wave body and a plane where the periphery of an end portion of the covered unit is located.

12. The covered stent according to claim 10, wherein the distance from the vertex of the first wave crest to the plane where the periphery of the end portion of the covered unit close to the bare unit is located is $H_2$, and a distance from a vertex of the third wave crest to the plane where the periphery of the end portion of the covered unit close to the bare unit is located is $H_3$, where $H_2/H_3$ is more than or equal to 0.8 and less than or equal to 1.2.

13. The covered stent according to claim 10, wherein a radius of the periphery of the end portion of the covered unit close to the bare unit is $D_1$, a radial distance from the vertex of the first wave crest to the central axis is $D_2$, and a radial distance from the vertex of the third wave crest to the central axis is $D_3$, where $D_3>D_1>D_2$; and $D_3-D_1=D_1-D_2$.

14. The covered stent according to claim 10, wherein the upright wave body further comprises a second wave rod for connecting the second wave crest with the second wave trough, and a third connecting segment connected at the second wave crest.

15. The covered stent according to claim 6, wherein a wire diameter of the upright wave body is $d_1$, and a wire diameter of the inward-tilting wave body is $d_2$, where $d_2/d_1$ is more than or equal to 0.2 and less than or equal to 0.9.

* * * * *